United States Patent [19]

Schäfer et al.

[11] 4,321,394
[45] Mar. 23, 1982

[54] PROCESS FOR THE PRODUCTION OF ADDITION COMPOUNDS OF CARBODIIMIDES AND COMPOUNDS CONTAINING HYDROXYL GROUPS

[75] Inventors: Walter Schäfer, Cologne; Kuno Wagner, Leverkusen; Kurt Findeisen, Odenthal, all of Fed. Rep. of Germany

[73] Assignee: Bayer Aktiengesellschaft, Leverkusen, Fed. Rep. of Germany

[21] Appl. No.: 190,103

[22] Filed: Sep. 24, 1980

[30] Foreign Application Priority Data

Oct. 11, 1979 [DE] Fed. Rep. of Germany ....... 2941253

[51] Int. Cl.³ .......................................... C07D 263/08
[52] U.S. Cl. .................................. 548/234; 260/404; 260/453.9; 260/944; 556/425; 564/252
[58] Field of Search ............................ 260/453.9, 404; 556/425; 548/234

[56] References Cited

U.S. PATENT DOCUMENTS

| | | | |
|---|---|---|---|
| 2,039,514 | 5/1936 | Battegay | 260/453.9 |
| 3,360,534 | 12/1967 | Odo et al. | 260/453.9 X |
| 3,670,022 | 6/1972 | Schaefer | 260/453.9 |

FOREIGN PATENT DOCUMENTS

956499  1/1957  Fed. Rep. of Germany ...... 548/234

Primary Examiner—Robert V. Hines
Attorney, Agent, or Firm—Gene Harsh; Joseph C. Gil

[57] ABSTRACT

The instant invention is directed to a process for the production of addition compounds of compounds containing hydroxyl groups and carbodiimides substantially free from isocyanate groups, comprising reacting the reactants in the presence of from 0.01 to 3% by weight, based on the reaction mixture, of a metal catalyst, the improvement wherein a tin compound is used as said metal catalyst.

8 Claims, No Drawings

PROCESS FOR THE PRODUCTION OF ADDITION COMPOUNDS OF CARBODIIMIDES AND COMPOUNDS CONTAINING HYDROXYL GROUPS

BACKGROUND OF THE INVENTION

This invention relates to an improved process for reacting compounds containing hydroxyl groups with carbodiimides. The improvement lies in the use of Sn(II) and Sn(IV) compounds as catalysts for the addition reaction.

It is known that addition compounds of equivalent quantities of hydroxyl compounds and carbodiimides, particularly, isourea ethers, are valuable textile auxiliaries and useful stabilizers. However, the reaction of alcohols with carbodiimides only takes place under energy-consuming conditions, generally at temperatures above 150° C. Although it is known from German Pat. No. 956,499 that the reaction of carbodiimides with alcohols to form isourea ethers is catalyzed by copper salts, this process has the serious disadvantage that the copper salts give rise to the formation of deep-colored crude products which have to be purified for many applications, in particular, in cases where they are to be used as textile auxiliaries.

Accordingly, the object of the present invention is to find an improved process in which the addition product of carbodiimide and hydroxyl compound may be used for the purposes mentioned above without any need for purification after the reaction.

It has now been found that reaction products of this type particularly isourea ethers and, optionally, their re-arrangement products, may be produced at temperatures as low as 25° to 150° C., provided that the carbodiimide and the hydroxyl compound are reacted in the presence of catalytic quantities of Sn(II) and Sn(IV) compounds. The crude products obtained by the process according to the invention are not colored and may be used without any need for purification. This is of particular advantage in cases where the product formed is a polymeric substance.

DESCRIPTION OF THE INVENTION

Accordingly, the present invention relates to a process for the production of addition compounds of compounds containing hydroxyl groups and carbodiimides substantially free from NCO groups, comprising reacting the components in the presence of from 0.01 to 3% by weight, based on the reaction mixture, of a metal catalyst, preferably at a temperature in the range from 25° to 150° C., the improvement wherein an inorganic and/or preferably organic tin compound are used as said metal catalyst.

Sn(II) compounds suitable for the process according to the invention are, for example, salts with $C_1$-$C_{25}$ carboxylic acids, such as tin(II)acetate, tin(II)oleate, tin(II)stearate, tin(II)octoate, tin(II)-(2-ethyl hexoate) and tin(II)laurate; Sn $(OH_2)$; $SnCl_2$; $SnF_2$, $SnBr_2$; $SnSO_4$ or even the products obtained by dissolving metallic tin in inorganic acids.

Another preferred class of catalysts are Sn(IV) compounds (such as dibutyl tin oxide or dibutyl tin chloride), and the dialkyl tin salts of carboxylic acids (such as dibutyl tin diacetate, dibutyl tin dilaurate, dibutyl tin maleate or dioctyl tin diacetate). However, it is also preferred to use complex compounds of Sn(II) or Sn(IV) salts, particularly, those of organic acids, with formamidines and quanidines, for example, the complex of Sn(II)ethyl hexoate and tetramethyl quanidine.

Examples of suitable starting compounds for producing the isourea ethers are carbodiimides corresponding to the following formula:

$$R-N=C=N-R'$$

in which R and R' which may be the same or different, represent an (optionally branched) $C_1$-$C_{20}$ alkyl radical, $C_4$-$C_{15}$ cycloalkyl radical, $C_6$-$C_{15}$ aryl radical or $C_7$-$C_{15}$ aralkyl radical. Examples of these compounds include diisopropyl carbodiimide; N-n-butyl-N'-cyclohexyl carbodiimide; N,N'-dicyclohexyl carbodiimide; N-t-butyl-N'-cyclohexyl carbodiimide, N-cyclohexyl-N'-phenyl carbodiimide, N-methyl-N'-t-butyl carbodiimide; N-t-butyl-N'-phenyl carbodiimide and N,N'-diphenyl carbodiimide.

It is also possible to use the polycarbodiimides obtainable from polyisocyanates using phospholine oxide as catalyst. The production of polycarbodiimides such as these is described, for example, in U.S. Pat. No. 2,941,966. The polyisocyanates which may be used for this purpose are aliphatic, cycloaliphatic, araliphatic, aromatic and heterocyclic polyisocyanates of the type described, for example, by W. Siefken in Justus Liebigs Annalen der Chemie, 562, pages 75 to 136, for example, those corresponding to the following formula $$Q\,(NCO)_n$$

in which
$n=2$–$4$, preferably 2, and
Q is an aliphatic hydrocarbon radical containing from 2 to 18, preferably from 6 to 10, carbon atoms; a cycloaliphatic hydrocarbon radical containing from 4 to 15, preferably from 5 to 10, carbon atoms; an aromatic hydrocarbon radical containing from 6 to 15, preferably from 6 to 13, carbon atoms or an araliphatic hydrocarbon radical containing from 8 to 15, preferably from 8 to 13 carbon atoms. Examples include ethylene diisocyanate; 1,4-tetramethylene diisocyanate; 1,6-hexamethylene diisocyanate; 1,12-dodecane diisocyanate; cyclobutane-1,3-diisocyanate; cyclohexane-1,3- and 1,4-diisocyanate and mixtures of these isomers; 1-isocyanato-3,5-trimethyl-5-isocyanatomethyl cyclohexane (German Auslegeschrift No. 1,202,785 or U.S. Pat. No. 3,401,190); 2,4- and 2,6-hexahydrotolylene diisocyanate and mixtures of these isomers; hexahydro-1,3- and/or 1,4-phenylene diisocyanate; perhydro-2,4'- and/or 4,4'-diphenyl methane diisocyanate; 1,3- and 1,4-phenylene diisocyanate; 2,4- and 2,6-tolylene diisocyanate and mixtures of these isomers; diphenyl methane-2,4'- and/or 4,4'-diisocyanate; and naphthylene-1,5-diisocyanate.

It is also possible to use the isocyanate group-containing distillation residues obtained in the commercial production of isocyanates, which may be used in solution in one or more of the above-mentioned polyisocyanates. Mixtures of the above-mentioned polyisocyanates may also be used.

It is also possible in principle to use aliphatic or aromatic diisocyanates of the type which are obtained by reacting excess diisocyanate with difunctional compounds containing hydroxyl or amine groups and which, in practical polyurethane chemistry, are referred to either as "modified isocyanates" or as "isocyanate prepolymers".

In the production of the polycarbodiimide, a chain terminator is preferably added to the reaction mixture of polyisocyanate and phospholine oxide in a molar ratio (based on the polyisocyanate) of less than 1:1 in order to regulate the molecular weight of the polycarbodiimide. Examples of suitable chain terminators are methanol, ethanol, cyclohexanol, ethyl amine, aniline, phenyl or tolyl isocyanate.

The second component required for producing the isourea ethers may be a hydroxyl compound corresponding to the following general formula:

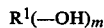

$$R^1(-OH)_m$$

in which the radical $R^1$ may be aliphatic, cycloaliphatic, araliphatic or aromatic or even heterocyclic and m is an integer of preferably from 1 to 10, in particular, 1 to 4.

Aliphatic radicals $R^1$ are straight or branched chain, saturated or unsaturated hydrocarbon radicals preferably containing from 1 to 25 carbon atoms and up to two double bonds or one triple bond; or cycloaliphatic radicals with 5, 6, 7, 8, 10, or 12 carbon atoms in the ring system which may even be substituted, (for example, by $C_6-C_{20}$ aryl radicals, preferably a phenyl and naphthyl radical; by $C_6-C_{10}$ aroxy radicals, preferably a phenoxy radical; $C_1-C_6$ alkoxy radicals; nitro groups, halogen-fluorine, chlorine, bromine, iodine; $C_1-C_6$ acyl; $C_1-C_6$ alkyl mercapto; $C_6-C_{20}$ aryl mercapto; cyano; $C_1-C_{12}$ carboxylic ester; carbonamide; $C_1-C_8$ dialkyl amino or $C_1-C_6$ acyl amino radicals).

Suitable aromatic radicals $R^1$ are aromatic hydrocarbon radicals containing up to 20 carbon atoms, preferably from 6 to 14 carbon atoms and, more preferably, up to 10 carbon atoms (most preferably, phenyl and naphthyl radicals) in the ring system. The aromatic radicals $R^1$ may, for example, contain the following substituents: alkyl, dialkylamino and alkoxy radicals containing from 1 to 12, preferably 1 to 6, carbon atoms; aryl and aroxy groups, preferably phenyl and phenoxy radicals; halogen (preferably, fluorine, chlorine, bromine); —CHO; carboxylic ester groups; aliphatic radicals containing from 1 to 12 and preferably from 1 to 6 carbon atoms; phenyl or benzyl radicals; carbonamide groups and alkyl sulfonyl groups containing from 1 to 12 and preferably from 1 to 6 carbon atoms; and aryl sulfonyl groups (preferably phenyl sulfonyl). The aromatic radical may also contain sulfonic ester groups, for example, with aliphatic radicals containing from 1 to 12 and preferably from 1 to 6 carbon atoms, phenyl or benzyl. Sulfonamide groups or acyl groups may also be present. They in turn may contain aliphatic radicals containing from 2 to 12 and preferably from 2 to 6 carbon atoms, or benzoyl groups, cyano, alkyl mercapto or acyl mercapto groups containing from 1 to 12 and preferably from 2 to 6 carbon atoms, aryl mercapto (preferably phenyl mercapto) groups and one to two $NO_2$-groups.

Preferred heterocyclic radicals $R^1$ are 5-, 6- or 7-membered ring systems containing one or more hetero atoms, such as, oxygen, nitrogen or sulfur, in the ring system.

Other suitable compounds of the formula $R^1(-OH)_m$ are phenols and alcohols containing several hydroxyl groups, such as, hydroquinone, pyrocatechol, resorcinol, cellulose, ethylene glycol, 1,2- and 1,3-propylene glycol, 1,4- and 2,3-butylene glycol, 1,5-pentane diol, 1,6-hexane diol, 1,8-octane diol, neopentyl glycol, 1,4-bis-hydroxy methyl cyclohexane, 2-methyl-1,3-propane diol, dibromobutene diol (U.S. Pat. No. 3,723,392), glycerol, trimethylol propane, 1,2,6-hexane triol, trimethylol ethane, pentaerythritol, quinitol, mannitol and sorbitol, castor oil, diethylene glycol, triethylene glycol, tetraethylene glycol, higher polyethylene glycols having a molecular weight of up to 400, dipropylene glycol, higher polypropylene glycols having a molecular weight of up to 400, dibutylene glycol, higher polybutylene glycols having a molecular weight of up to 400, 4,4′-dihydroxy diphenyl propane, dihydroxy methyl hydroquinone, ethanolamine, diethanolamine, N-methyl diethanolamine, triethanolamine and 3-aminopropanol.

According to the invention, other suitable low molecular weight polyols are mixtures of hydroxy aldehydes and hydroxy ketones ("formose") and the polyhydric alcohols obtained therefrom by reduction ("formitol") of the type formed in the autocondensation of formaldehyde hydrate in the presence of metal compounds as catalyst and compounds capable of enediol formation as co-catalyst (German Offenlegungsschriften Nos. 2,639,084; 2,714,084; 2,714,104; 2,721,186; 2,738,154 and 2,738,512).

According to the invention, however, the reactant for the carbodiimide may also be selected from relatively high molecular weight polyhydroxyl compounds, particularly, compounds containing from 2 to 8 hydroxyl groups, especially those having a molecular weight in the range from 800 to 10,000 and preferably in the range from 1000 to 6000, for example, polyesters, polyethers, polythioethers, polyacetals, polycarbonates, and polyester amides containing at least 2, generally from 2 to 8, but preferably from 2 to 4 hydroxyl groups, of the type known per se for the production of homogeneous and cellular polyurethanes.

The polyesters containing hydroxyl groups which may be used in accordance with the invention are, for example, reaction products of polyhydric, preferably dihydric and, optionally, even trihydric alcohols with polybasic, preferably dibasic carboxylic acids, Instead of using the free polycarboxylic acids, it is also possible to use the corresponding polycarboxylic acid anhydrides or corresponding polycarboxylic acid esters of lower alcohols or mixtures thereof for producing the polyesters. The polycarboxylic acids may be aliphatic, cycloaliphatic, aromatic and/or heterocyclic and may optionally be substituted, for example, by halogen atoms, and/or unsaturated.

The following carboxylic acids and their derivatives may be used: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimerized and trimerized unsaturated fatty acids, which may be in admixture with monomeric unsaturated fatty acids (such as oleic acid), terephthalic acid dimethyl ester and terephthalic acid-bis-glycol ester. Suitable polyhydric alcohols are, for example, ethylene glycol, 1,2- and 1,3-propylene glycol, 1,4- and 2,3-butylene glycol, 1,6-hexane diol, 1,8-octane diol, neopentyl glycol, 1,4-bis-hydroxy methyl cyclohexane, 2-methyl-1,3-propane diol, glycerol, trimethylol propane, 1,2,6-hexane triol, 1,2,4-butane triol, trimethylol ethane, pentaerythritol, quinitol, mannitol and sorbitol, formitol, methyl glycoside, also diethylene glycol, triethylene glycol, tetraethylene glycol and higher polyethylene glycols, dipropylene glycol and higher polypropylene glycols, dibutylene glycol and higher polybutylene glycols. The polyesters may also contain terminal carboxyl groups. Polyesters of lactones (for example, ε-caprolactone), or of hydroxy carboxylic acids (for example, ω-hydroxy caproic acid), may also be used.

The polyesters containing at least two, generally two to eight and preferably two to three hydroxyl groups which may be used in accordance with the invention are obtained, for example, by polymerizing epoxides (such as ethylene oxide, propylene oxide, butylene oxide, tetrahydrofuran, styrene oxide or epichlorohydrin) on their own, for example, in the presence of Lewis catalysts (such as boron trifluoride), or by adding these epoxides (preferably ethylene oxide and propylene oxide), either in admixture or successively, with starting components containing reactive hydrogen atoms. Examples of components containing reactive hydrogen atoms include water, alcohols, ammonia or amines. Some specific examples include ethylene glycol, 1,3- or 1,2-propylene glycol, trimethylol propane, glycerol, sorbitol, 4,4'-dihydroxy diphenyl propane, aniline, ethanolamine or ethylene diamine. Sucrose polyethers (German Auslegeschriften Nos. 1,176,358 and 1,064,938) and formitol- or formose-started polyethers (German Offenlegungsschriften Nos. 2,639,083 and 2,737,951) may also be used in accordance with the invention. In many cases, it is preferred to use polyethers which predominantly contain primary hydroxyl groups (up to 90% by weight, based on all of the hydroxyl groups present in the polyether). Polybutadienes containing hydroxyl groups may also be used in accordance with the invention.

Among the polythioethers, reference is made in particular to the condensation products of thiodiglycol on its own and/or with other glycols, dicarboxylic acids, formaldehyde, aminocarboxylic acids or aminoalcohols. Depending on the co-components, the products in question are, for example, polythio mixed ethers, polythioether esters or polythioether ester amides.

Suitable polyacetals are, for example, the compounds obtainable from glycols, such as diethylene glycol, triethylene glycol, 4,4'-dioxethoxy diphenyl dimethyl methane, hexane diol and formaldehyde. Polyacetals suitable for use in accordance with the invention may also be produced by polymerizing cyclic acetals such as trioxane (German Offenlegungsschrift No. 1,694,128).

Suitable polycarbonates containing hydroxyl groups may be produced, for example, by reacting diols (such as 1,3-propane diol, 1,4-butane diol and/or 1,6-hexane diol, diethylene glycol, triethylene glycol, tetraethylene glycol or thiodiglycol), with diaryl carbonates, for example, diphenyl carbonate, or phosgene (German Auslegeschriften Nos. 1,694,080; 1,915,908 and 2,221,751; and German Offenlegungsschrift No. 2,605,024).

Suitable polyester amides and polyamides include, for example, the predominantly linear condensates obtained from polybasic (saturated or unsaturated) carboxylic acids (or their anhydrides) and polyhydric (saturated or unsaturated) aminoalcohols, diamines, polyamines and mixtures thereof.

Polyhydroxyl compounds already containing urethane or urea groups and optionally modified natural polyols, such as castor oil, or carbohydrates (for example, starch), may also be used. Addition products of alkylene oxides with phenol-formaldehyde resins or even with urea-formaldehyde resins may also be used in accordance with the invention.

Representatives of the above-mentioned compounds used in accordance with the invention are described in *High Polymers*, Vol. XVI, "Polyurethanes, Chemistry and Technology" by Saunders-Frisch, Interscience Publishers, New York/London, Vol. I, 1962, pages 32–42 and pages 44–54, and Vol. II, 1964, pages 5–6 and 198–199 and in Kunststoff-Handbuch, Vol. VII, Vieweg-Hochtlen, Carl-Hanser-Verlag, Munich, 1966, for example, on pages 45–71.

Other suitable hydroxyl components are polyhydroxy organopolysiloxanes, for example,

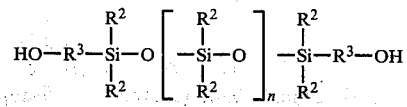

in which $R^3$ represents a difunctional hydrocarbon radical containing from 1 to 6 carbon atoms, $R^2$ represents a monofunctional alkyl radical containing up to 4 carbon atoms, and n is 0 or an integer of from 1 to 10,000.

The component $R^1$—OH may also be formed by those compounds in which $R^1$ is a substituted phosphorus radical. Preferred radicals of this type are dialkoxy phosphine radicals, such as the dimethoxy phosphine, diethoxy phosphine, dipropoxy phosphine, dibutoxy phosphine, bis-(2,2,2-trifluoroethoxy)-phosphine, bis-(2-hydroxypropoxy)-phosphine, bis-(2-chloroethoxy)-phosphine, bis-(2-fluoroethoxy)-phosphine and diphenoxy phosphine radical.

The process according to the invention is preferably carried out by combining the hydroxyl compound and the carbodiimide in the required molar ratio (preferably in substantially equivalent quantities) and subsequently adding the Sn-compound, preferably in quantities of from 1/10 to 1/1000 mole, based on 1 mole of carbodiimide. If there is no evidence of any reaction at room temperature, which may readily be verified in a preliminary test through the disappearance of the carbodiimide band (2120 cm$^{-1}$) in the IR-spectrum, the reaction mixture is slowly heated, but preferably to no higher than 140° C. The crude products of isourea ethers obtained in this way show no coloration and do not have to be purified.

The reaction may be carried out either in the absence or in the presence of a solvent which is inert to carbodiimide and hydroxyl compound.

Suitable solvents are, for example, toluene, o- and m-dichlorobenzene, nitrobenzene, methylene chloride, ethyl acetate, acetone, methyl ethyl ketone, acetonitrile, tetrahydrofuran, dioxane, dimethyl formamide, dimethyl sulfoxide, sulfolan and hexamethyl phosphoric acid triamide.

Both the monoisourea ethers and the polyisourea ethers may, for example, be used as stabilizers for polyesters (German Offlenegungsschrift No. 2,528,589) and as textile auxiliaries (German Pat. No. 1,011,869). The products of the process may also be used as intermediate products for further syntheses, for example, of plant protection agents and medicaments. In addition, isourea ethers are alkylating agents (Tetrahedron Letters (1974) 143) and also preliminary stages for the olefinization of hydroxyl compounds (CHimia 29, 520 (1975)).

EXAMPLE 1

46 g of ethanol are added to 194 g of diphenyl carbodiimide and the solution heated to 60° C. After 0.05 g of tin(II)-(2-ethyl hexoate) have been added to the reaction solution, the isourea is formed quantitatively in 3 hours. In the IR-spectrum, the carbodiimide band at 2120 cm$^{-1}$ disappears and the isourea ether band appears in its place at 1655 cm$^{-1}$. Bp$_{0.07}$=122° C.

EXAMPLE 2 (Comparison)

46 g of ethanol are added to 194 g of diphenyl carbodiimide and the solution subsequently heated to 60° C. After 3 hours, there is no evidence of any reaction.

EXAMPLE 3

32 g of methanol, 206 g of dicyclohexyl carbodiimide and 0.1 g of Sn(II)-(2-ethyl hexoate) are combined and the reaction mixture subsequently heated for 2 hours to 80° C., the carbodiimide band (2120 cm$^{-1}$) disappearing completely.

214 g (89% of the theoretical) of the isourea ether can be distilled off from the crude product at 102° to 104° C. under a pressure of 0.1 Torr.

EXAMPLE 4

40 mg of di-(n-butyl)-Sn(II)-dilaurate are added to 9.7 g of diphenyl carbodiimide and 4.6 g of ethanol dissolved in 40 ml of DMF. The reaction mixture reacts over a period of 1 hour at 52° C. to form the isourea ether.

EXAMPLE 5

194 g of diphenyl carbodiimide, 31 g of ethylene glycol and 0.05 g of Sn(II)-(2-ethyl hexoate) are dissolved in 200 g of xylene. The reaction solution is heated to reflux temperature, diphenyl urea being precipitated. Concentration of the xylene solution gives 102 g (86% of the theoretical) of 2-phenyl imino-3-phenyl oxazolidine. Mp: 115° to 117° C.

EXAMPLE 6

222 g of ditolyl carbodiimide, 1000 g of a linear polypropylene glycol (hydroxyl number 56) and 0.1 g of Sn(II) (2-ethyl hexoate) are stirred together. The reaction mixture is then heated to 120° C. In the IR-spectrum, the carbodiimide band disappears and the bis-(N,N'-ditolyl isourea)-derivative of the polypropylene oxide diol is formed.

EXAMPLE 7

16.7 g of bis-(3,4-dichlorophenyl)-carbodiimide, 5.9 g of benzyl alcohol, 60 ml of toluene and 0.1 g of Sn(II)-(2-ethyl hexoate) are combined and the reaction mixture subsequently heated for 30 minutes to 70° C. After the reaction mixture has been concentrated, the O-benzyl-N,N'-di-(3,4-dichlorophenyl)-isourea crystallizes out substantially quantitatively. Mp: 95° to 97° C.

EXAMPLE 8

10.3 g of dicyclohexyl carbodiimide, 5.35 g of cyclohexanol, 60 ml of xylene and 0.1 g of Sn(II)-(2-ethyl hexoate) are combined and the reaction mixture subsequently heated for 2 hours to 130° C., the carbodiimide band at 2120 cm$^{-1}$ disappearing completely. After the reaction mixutre has been concentrated, the O,N,N-tricyclohexyl isourea crystallizes out. Mp: 55° to 57° C.

EXAMPLE 9

(a) 12.7 g of di-p-tolyl carbodiimide, 5.18 g of phenol, 60 ml of toluene and 0.1 g of Sn(II)-(2-ethyl hexoate) are combined and the reaction mixture is subsequently heated for 2 hours to 110° C., the carbodiimide band at 2120 cm$^{-1}$ disappearing completely. After the reaction mixture has been concentrated, the O-phenyl-N,N'-di-p-tolyl isourea crystallizes out. Mp: 112° to 113° C.

(b) If the mixture prepared in accordance with (a) is heated without any Sn(II)-(2-ethyl hexoate) for comparison, there is no significant reaction and the carbodiimide band at 2120 cm$^{-1}$ remains intact.

EXAMPLE 10

(a) 19.4 g of diphenyl carbodiimide, 18 g of diethyl phosphite and 0.1 g of Sn(II)-(2-ethyl hexoate) are combined and the reaction mixture is subsequently heated for 1.5 hours to 100° C. After cooling, the 1:1 adduct crystallizes out and, after recrystallization from petroleum ether, has a melting point of 112° C.

(b) If the mixture prepared in accordance with (a) is heated to 100° C. without any Sn(II)-(2-ethyl hexoate), there is no evidence of any reaction.

EXAMPLE 11

Into a mixture of 8.9 g (0.1 mol) dimethylethanolamine and 0.05 g Sn-II-(2-ethylhexoate) in 100 ml of dry toluene is added dropwise a solution of 33.2 g (0.1 mol) bis-[3,4-di-chloro-phenyl]-carbodiimide in 100 ml of dry toluene while stirring at a temperature of 30° C. The reaction is exothermic. The reaction mixture is stirred further 30 minutes at 60° C. After being freed from volatiles at high vacuum (0.005 Torr) at 60° C., the iso-urea is obtained in nearly quantitative yield in the form of white crystals with a melting point of 76° C.

EXAMPLE 12

14.6 g (0.1 mol) di-anhydro-sorbit, 66.4 g (0.2 mol) bis-[3,4-dichlorophenyl]-carbodiimide and 0.05 g of Sn-II-(2-ethylhexoate) are dissolved in 200 ml of dioxane. The reaction mixture is stirred for 5 hours at 80° C. and then freed from solvent at a vacuum of 15 Torr/ 80° C. After washing the crude product with toluene 52 g of crystals of the iso-urea with a melting point of 132° C. are isolated.

EXAMPLE 13

56 g (0.1 mol) polyethylene glycol, 38.8 g (0.2 mol) diphenyl-carbodiimide and 0.05 g Sn-II-(2-ethyl-hexoate) are heated to 100° C. for 2 hours. The resulting iso-urea-derivative is a colourless resin with a viscosity of 50 Pa.s at 30° C.

EXAMPLE 14

50 g of a polycarbodiimide on the basis of isophorone-di-isocyanate with an average of about 4 carbodiimide-groups per molecule are dissolved with 0.05 g Sn-II-(2-ethyl-hexoate) in 100 ml of ethanol and refluxed for some hours. After disappearance of the carbodiimide absorption at 2120 cm$^{-1}$ the polyiso-urea solution is freed from solvent. The dry product has a melting range between 61° and 65° C. The starting material (polycarbodiimide) is produced from isophorone diisocyanate under catalysis of 1 weight percent of 1-methyl-, 1-phospha-cyclopentane-1-oxid ("phospholin oxide") by 2½ hours heating to 150°–160° C.

What is claimed is:

1. In a process for the production of addition compounds of compounds containing hydroxyl groups and carbodiimides substantially free from isocyanate groups, comprising reacting the reactants in the presence of from 0.01 to 3% by weight, based on the reaction mixture, of a metal catalyst, the improvement wherein a tin compound is used as said metal catalyst.

2. The process of claim 1, wherein compounds of divalent tin are used as said catalyst.

3. The process of claim 2, wherein salts of divalent tin with $C_1$–$C_{25}$ carboxylic acids are used as said catalyst.

4. The process of claim 3, wherein Sn(II)-(2-ethyl hexoate) is used as said catalyst.

5. The process of claim 1, wherein compounds of tetravalent tin are used as said catalyst.

6. The process of claim 5, wherein dibutyl tin dilaurate is used as said catalyst.

7. The process of claim 1, wherein the reaction is carried out at temperatures in the range from 25° C. to 150° C.

8. The process of claim 1, wherein said tin compound is organic and/or inorganic.

* * * * *